United States Patent
Ahn et al.

(10) Patent No.: US 11,951,145 B2
(45) Date of Patent: Apr. 9, 2024

(54) **COMPOSITION FOR PREVENTING OR TREATING CANCER COMPRISING EXTRACTS OF ANEMONE RADDEANA, *LONICERA* SPECIES, AND ARALIA ELATA CONTAINING HIGH CONCENTRATION OF ANTITUMOR SAPONINS, AND METHOD FOR PREPARING SAME**

(71) Applicant: Ju Youn Back, Seoul (KR)

(72) Inventors: Byung Zun Ahn, Daejeon (KR); Jae Seung Roh, Gumi-si (KR)

(73) Assignee: Ju Youn Back, Seoul (KR)

( * ) Notice: Subject to any disclaimer, the term of this patent is extended or adjusted under 35 U.S.C. 154(b) by 0 days.

(21) Appl. No.: 17/053,040

(22) PCT Filed: Mar. 12, 2019

(86) PCT No.: PCT/KR2019/002861
§ 371 (c)(1),
(2) Date: Nov. 4, 2020

(87) PCT Pub. No.: WO2019/212140
PCT Pub. Date: Nov. 7, 2019

(65) Prior Publication Data
US 2021/0236576 A1 Aug. 5, 2021

(30) Foreign Application Priority Data
May 4, 2018 (KR) .......................... 10-2018-0052100

(51) Int. Cl.
| A61K 36/71 | (2006.01) |
| A61K 31/704 | (2006.01) |
| A61K 36/25 | (2006.01) |
| A61K 36/355 | (2006.01) |
| A61P 35/00 | (2006.01) |

(52) U.S. Cl.
CPC ............ *A61K 36/71* (2013.01); *A61K 31/704* (2013.01); *A61K 36/25* (2013.01); *A61K 36/355* (2013.01); *A61P 35/00* (2018.01); *A61K 2236/15* (2013.01); *A61K 2236/19* (2013.01); *A61K 2236/331* (2013.01); *A61K 2236/39* (2013.01); *A61K 2236/55* (2013.01)

(58) Field of Classification Search
None
See application file for complete search history.

(56) References Cited

U.S. PATENT DOCUMENTS

| 2004/0067263 A1 | 4/2004 | Liu et al. |
| 2006/0216366 A1 | 9/2006 | Karl Tsim et al. |
| 2008/0268072 A1 | 10/2008 | Kim et al. |
| 2012/0015056 A1 | 1/2012 | Lee |

FOREIGN PATENT DOCUMENTS

| CN | 101085804 A | * | 12/2007 |
| CN | 101085804 A | | 12/2007 |
| CN | 101157714 A | | 4/2008 |
| CN | 101229212 A | | 7/2008 |
| CN | 102451205 A | | 5/2012 |
| CN | 102603856 A | | 7/2012 |
| CN | 105641078 A | | 6/2016 |
| KR | 10-2006-0047198 A | | 5/2006 |
| KR | 10-2006-0092158 A | | 8/2006 |
| KR | 20060092158 | * | 8/2006 |
| KR | 10-0628334 B1 | | 9/2006 |
| KR | 10-1218340 B1 | | 1/2013 |
| TN | 1280881 B | * | 5/2007 |
| WO | 2002-067962 A1 | | 9/2002 |

OTHER PUBLICATIONS

CN101085804A translated doc (Year: 2007).*
Mingkui (Anti-tumor Activity of Crude Saponin from Anemone raddeana Regel, Chin J Appl Environ Biol, 2008, 14(3):378-382), (Year: 2008).*
TW1280881B translated doc (Year: 2007).*
Guo et. al. (Chemistry and pharmacology of the herb pair Flos Lonicerae japonicae-Forsythiae fructus, Chinese Medicine, 2015, 10:16) (Year: 2015).*
KR20060092158 translated doc (Year: 2006).*
International Search Report issued for International Application No. PCT/KR2019/002861 dated Jun. 24, 2019, 4 pages.
Park, K. I. et al., Apoptosis by the Purified Korea Lonicera Japonica T. in Human Lung Cancer Cells., Korean Journal of Veterinary Science, 2011, vol. 51:119-120.
Lu J. et al., Structure elucidation of two triterpenoid saponins from rhizome of Anemone raddeana Regel. Fitoterapia. Sep. 2009; 80(6):345-348.
Bang, S.C., et al., Antitumor activity of Pulsatilla koreana saponins and their structure-activity relationship, Chem. Pharm. Bull. (Tokyo), 2005, 53(11), 1451-1454.
Kim, J.S., et al., Phytochemical Studies on Lonicera Caulis(1)- Sterols and Triterpenoids, Kor. J. Pharmacogn., 2009, 40(4), 319-325.

(Continued)

*Primary Examiner* — Terry A McKelvey
*Assistant Examiner* — Jacob A Boeckelman
(74) *Attorney, Agent, or Firm* — ROTHWELL, FIGG, ERNST & MANBECK, P.C.

(57) ABSTRACT

The present invention relates to a composition for preventing or treating cancer, comprising extracts of *Anemone raddeana* and *Lonicera* species containing a high concentration of antitumor saponins, and a method for preparing the same, wherein saponins contained in the extracts of *Anemone raddeana* and *Lonicera* species, are converted to anticancer saponins having high antitumor activity, thereby producing extracts containing a high concentration of the antitumor saponins, and the extracts thus prepared have been confirmed to show desirable antitumor activity. Accordingly, the extracts containing a high concentration of antitumor saponins of the present invention are promising for use in the development of drugs for cancer treatment.

5 Claims, 1 Drawing Sheet

(56) References Cited

OTHER PUBLICATIONS

Sun, Y.X., et al., Phytochemicals and bioactivities of Anemone raddeana Regel: a review, Pharmazie, 2011, 66(11), 813-821.
Yun, K.J., et al., Effects of Hot Aqueous and Ethanol Extract from Lonicera japonica Flos on NO and PGE2 in Macrophage, The Journal of Korean Acupuncture & Moxibustion Society, 2012, 29(1):67-74.
Zhang Y., et al., Studies on cytotoxic triterpene saponins from the leaves of Aralia elata. Food Chem. May 1, 2013;138(1):208-13.
Extended European Search Report issued in corresponding European Patent Application No. 19796547.8 dated Jan. 24, 2022, 8 pages.

* cited by examiner

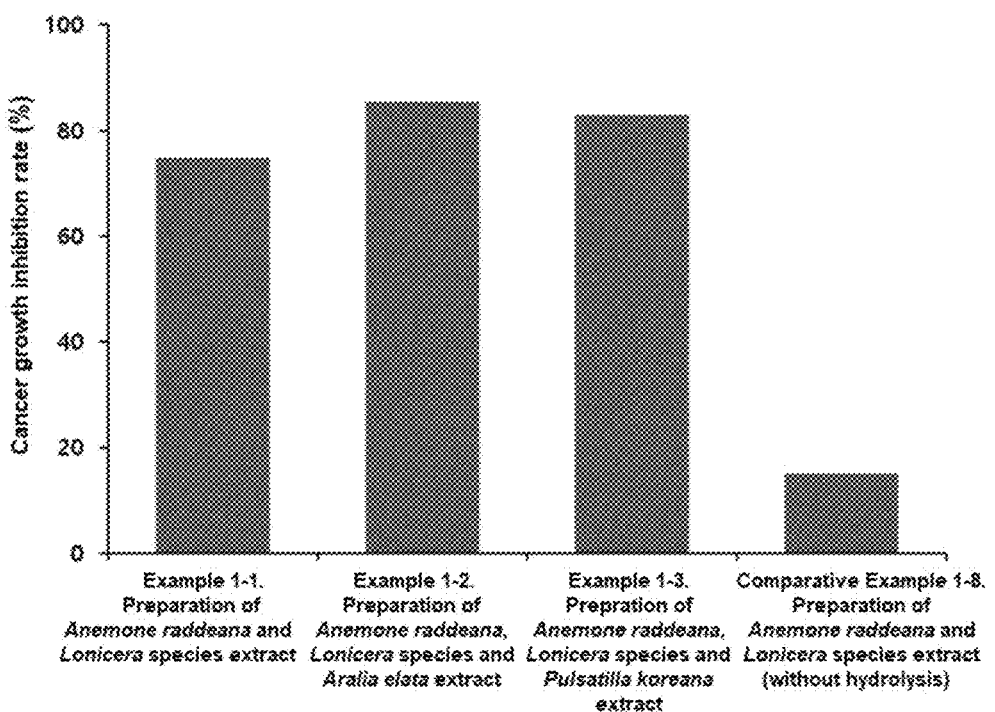

COMPOSITION FOR PREVENTING OR TREATING CANCER COMPRISING EXTRACTS OF ANEMONE RADDEANA, *LONICERA* SPECIES, AND ARALIA ELATA CONTAINING HIGH CONCENTRATION OF ANTITUMOR SAPONINS, AND METHOD FOR PREPARING SAME

CROSS-REFERENCE TO RELATED APPLICATION(S)

This application is a 35 U.S.C. 371 National Phase Entry Application from PCT/KR2019/002861 filed on Mar. 12, 2019, designating the United States, which claims the benefits of filing date of Korean Patent Application No. 10-2018-0052100 filed on May 4, 2018, the entire contents of which are incorporated herein by reference.

TECHNICAL FIELD

The present disclosure relates to a composition comprising an *Anemone raddeana* and *Lonicera* species extract for prevention or treatment of cancer and, more particularly, to a composition for prevention or treatment of cancer, the composition comprising an *Anemone raddeana* and *Lonicera* species extract containing a high concentration of anticancer saponins, alone or in combination with an *Aralia elata* extract or a *Pulsatilla* sp. extract, and a preparation method therefor.

BACKGROUND ART

Cancers, academically called neoplasia, are characterized by uncontrolled cell growth. A group of cells that have undergone abnormal growth forms a mass, called a tumor, which invades to neighboring tissues and, in severe cases, may be metastasized to other organs in the body. Cancers affect all tissues and organs across the body at various prevalence rates.

The types of cancer may be classified according to tissues and organs in which cancer cells first develop, and according to morphologies and origins of cancer cells. Lung cancer, gastric cancer, colorectal cancer, cervical cancer, and the like are often referred to on the basis of the organs in which the tumor is first developed. In addition, cancers may be largely divided into connective tissue tumors, epithelial tumors, adenocarcinoma, and the like in an aspect of the origin of cancer cells. In South Korea, the most common cancer is thyroid cancer, followed by gastric cancer, colorectal cancer, and lung cancer, in the order of incidence.

Among cancer therapies are aggressive therapies of removing cancer tissues solidified in the organs or killing cancer cells and palliative therapies of delaying the development of cancer cells to minimize side effects. For the early stage of cancer development, there are selectable options including the removal of tumors through surgery, chemotherapy, radiotherapy, and the like or the killing of cancer cells through chemical drugs, radiation, and the like.

For end-stage cancer patients, aggressive therapies have relatively serious side effects and thus, selection may be made of therapies for delaying the development of cancer cells to reduce side effects and improve the quality of life. In general, anticancer drugs, which account for anticancer chemotherapy belonging to aggressive therapies, include cytotoxic anticancer drugs for killing cancer cells with toxic substances, target cancer drugs that selectively act on cancer cells and new blood vessels around tissues, and the like (Jung GeunYoung, 2016).

Most anticancer drugs are medicines that show effects by acting on rapidly growing and dividing cancer cells, but cause side effects by attacking some normal cells that also show rapid growth and division. None of the therapeutic agents that have been developed thus far can completely cure cancer. Therefore, with respect to cancer treatment, there is a continuing need for the development of therapeutic agents having excellent anti-cancer effects.

Saponins are generic terms for glycosides widely distributed in plant kingdom and found in particular abundance in Ranunculaceae, Araliaceae, Dioscoreaceae, Leguminosae, Cucurbitaceae, Compositae, Rosaceae, Liliaceae, Rubiaceae, Rhamnaceae, and Caryophyllaceae.

Saponins contain one or more aglycone moieties based on a steroid, steroid alkaloid, or triterpene scaffold to which one or more sugar chains are attached (Bachran, C., et al., 2008). Saponins exhibit structural diversity according to the number of sugar chains attached to the aglycone and kinds of the sugar and can be divided into: monodesmosides in which the aglycone has a singly attached chain sets of sugars; and bisdesmosides in which there are two chain sets of sugars.

Saponins were reported to have various effects as anticancer agents and immune adjuvants on cancer cells. The first study in 1979 reported that the saponin Quil A prolonged the survival of a spontaneous leukemia mouse model (Ebbesen, P., et al., 1976). Since then, studies have been conducted into effects of various saponins, including ginseng saponins and *Bupleurum falcatum* saponins, on tumor cancers. It was reported that the saponin dioscin isolated from roots of *Polygonatum zanlanscianense* Pamp. induced apoptosis of cervical cancer cells and the saponin dioscin isolated from rhizomes of *Smilacina atropurpurea* exhibited potent cytotoxicity against various kinds of cancer cell lines. Saikosaponins, a kind of saponins, are triterpene saponins from *Bupleurum* sp. Plants. Saikosaponin-a has potent effects of inhibiting liver cancer cell lines and of promoting apoptosis of human breast cancer cell lines. Saikosaponin-b is cytotoxic against liver cancer cells. Julibrosides and derivatives thereof, which are saponins isolated from *Albizia julibrissin* barks, have cytotoxicity against liver cancer, cervical cancer, and breast cancer cell lines. In addition, anticancer activity was observed in soybean-derived saponins, ginseng-derived saponins, and avicins isolated *Acacia victoriae* native to Australia (Bachran, C., et al., 2008).

Bang, S. C., et al., 2005 isolated 17 different saponins from roots of *Pulsatilla* sp. native to Korea, revealing that six of them has anticancer activity. In addition, the six saponins were structurally analyzed to be monodesmosides having hederagenin, oleanolic acid, betulinic acid, and 23-hydroxybetulinic acid as aglycone moieties, with a free carboxylic group at position 28 and rhamnopyranosyl(1→2) arabinopyranosyl bound at position 3.

However, saponins having a free acidic functional group at position 28 are found in a small amount in nature and most exist in the form of glycosyl ester. Therefore, the ester group must be hydrolyzed to obtain saponins with a free acidic functional group at position 28, which are of anticancer activity.

Leading to the present disclosure, intensive and thorough research, conducted by the present inventors, into anticancer saponins from various plants, resulted in the finding that extracts from *Anemone raddeana* and *Lonicera* species are highly abundant in saponins exhibiting excellent anticancer activity.

As prior arts, Korean Patent number 1218340 discloses a composition for treatment of cancer, the composition comprising a saponin-containing *Lonicera japonica* extract and U.S. Patent No. 2004-0067263 A discloses a method for preparing an *Anemone raddeana* extract containing a raw saponin and a composition comprising the same for treating cancer. However, the compositions are different from in configuration from the composition of the present disclosure containing extracts from *Anemone raddeana* and *Lonicera* species which contain high concentration of anticancer saponins. Korean Patent number 0628334 discloses a method for preparing a saponin having an improved anticancer effect by enzymatically hydrolyzing saponin of Pulsatillaeradix, but does neither mention an *Anemone raddeana* and *Lonicera* species extract containing high concentrations of anticancer saponin nor anticancer effects thereof.

DETAILED DESCRIPTION OF THE INVENTION

Technical Problem

A purpose of the present disclosure is to provide a composition comprising an *Anemone raddeana* and *Lonicera* species extract highly rich in anticancer saponins for preventing or treating cancer and a preparation method therefor.

Technical Solution

The present disclosure pertains to a pharmaceutical composition comprising an *Anemone raddeana* and *Lonicera* species extract as an active ingredient for prevention or treatment of cancer, the extract being prepared through: i) a first step of adding distilled water to the plants and grinding the plants to give a medium of plants per se; ii) a second step of adding an organic solvent to the plants to give a plant extract; iii) a third step of combining the medium of plants per set in the first step with the plant extract in the second step and fermenting the combination at 37° C. while stirring; iv) a fourth step of adding an organic solvent to the fermented product obtained by fermentation in the third step to form fractions; v) a fifth step of subjecting the fractions of the forth step to column chromatography to acquire eluates; and vi) a sixth step of adding an organic solvent to the eluates of the fifth step to obtain fractions and drying the fractions.

The medium of plants per se may be prepared through steps of primarily grinding a plant in distilled water with the aid of a mixer; and secondarily grinding the plant by sonication.

The *Anemone raddeana* and *Lonicera* species extract may further include at least one selected from the group consisting of a medium of *Pulsatilla koreana* per se, a *Pulsatilla koreana* extract, and an *Aralia elata* extract.

The *Anemone raddeana* and *Lonicera* species extract may be 15 to 110 fold improved in anticancer saponin content.

The anticancer saponin may be at least one selected from the group consisting of hederagenin 3-O-β-D-glucopyranosyl-(1→4)-β-D-glucopyranosyl-(1→3)-α-L-rhamnopyranosyl-(1→2)-α-L-arabinopyranoside, oleanolic acid 3-O-α-L-rhamnopyranosyl-(1→2)-[β-D-glucopyranosyl-(1→4)]-α-L-arabinopyranoside, and hederagenin 3-O-β-D-glucopyranosyl-(1→3)-α-L-rhamnopyranosyl-(1→2)-α-L-arabinopyranoside.

The pharmaceutical composition may further comprise an anticancer agent.

The cancer may be a solid cancer.

Below, a detailed description will be given of the present disclosure.

The present disclosure pertains to a composition comprising an *Anemone raddeana* and *Lonicera* species extract as an active ingredient for prevention or treatment of cancer, the *Anemone raddeana* and *Lonicera* species extract being prepared through: i) a first step of adding distilled water to the plants and grinding the plants to give a medium of plants per se; ii) a second step of adding an organic solvent to the plants to give a plant extract; iii) a third step of combining the medium of plants per set in the first step with the plant extract in the second step and fermenting the combination at 37° C. while stirring; iv) a fourth step of adding an organic solvent to the fermented product obtained by fermentation in the third step to form fractions; v) a fifth step of subjecting the fractions of the fourth step to column chromatography to acquire eluates; and vi) a sixth step of adding an organic solvent to the eluates of the fifth step to obtain fractions and drying the fractions.

*Anemone raddeana* is a perennial herb belonging to the genus *Anemone* in the family Ranunculaceae and is native to China, Russian Far East, and Korea. Major active ingredients of *Anemone raddeana* include oleanane triterpenoids and glycosides thereof which are known to have pharmaceutically activities such as anti-inflammatory activity, anti-tumor activity, pain relief, anti-convulsant activity, etc. (Sun, Y. X., et al., 2011).

*Anemone raddeana* may be available in the form of a media of plant per se or a plant extract.

*Lonicera* species are perennial herbs belonging the family Caprifoliceae as exemplified by *Lonicera japonica, Lonicera macranthoides, Lonicera fulvotomentosa*, etc., and are known to contain the anticancer saponin hederagenin 3-O-β-D-glucopyranosyl-(1→4)-β-D-glucopyranosyl-(1→3)-α-L-rhamnopyranosyl-(1→2)-α-L-arabinopyranoside.

So long as it contains an anticancer saponin, any *Lonicera* species may be used. The *Lonicera* species preferably includes *Lonicera japonica, Lonicera macranthoides*, and *Lonicera fulvotomentosa*, with higher preference for *Lonicera japonica*.

Stems and flowers of *Lonicera japonica*, which are respectively named Lonicerae Folium and Lonicerae Flos, have been used as medicinal materials in folk remedies and in herbal medicine. *Lonicera japonica* contains flavonoids, iridoids, saponins, and other phenolic compounds, with iridoids found as a major constituent (Kim, J. S., et al., 2009) and the flower thereof was reported to have antiviral activity, antibacterial activity, anti-endotoxin activity, anti-inflammatory activity, immunopotentiation, anticancer activity, and so on (Yun, K. J., et al, 2012).

The *Lonicera* species may be available in the form of a medium of plant per se or a plant extract.

As used herein, the term "a medium of plant per se" refers to a medium made of a plant per se, which is used as a fermentation substrate and takes advantage of the ability of hydrolase present in plant cells to hydrolyze ester groups of saponins.

The medium of plant per se in the first step may be prepared by primarily grinding a plant in distilled water with a mixer; and secondarily grinding the primarily ground plant by sonication.

For preparation of the medium of plant per se, any plant may be available as long as it has a hydrolase present in the cells thereof and contains a saponin. Examples of the available plants include plants belonging to the families Ranunculaceae, Araliaceae, Dioscoreaceae, Leguminosae, Cucurbitaceae, Compositae, Rosaceae, Liliaceae, Rubiaceae, Rhamnaceae, and Caryophyllaceae, but are not limited thereto.

Preferably, the plant may be at least one selected from the group consisting of *Pulsatilla koreana, Pulsatilla chinensis, Pulsatilla cernua, Anemone raddeana, Aralia elata, Akebia quinata, Lonicera* species, and *Patrinia scabiosifolia*, more preferably from the group consisting of *Pulsatilla koreana, Anemone raddeana, Lonicera* species, and *Akebia quinata*, far more preferably from the group consisting of *Pulsatilla koreana* and *Anemone raddeana*, and most preferably *Anemone raddeana*.

As for the available plants, their roots, leaves, fruits, and seeds are useful for preparing a medium of plant per se. Preferable are roots and fruits of plants. For seeds rich in vegetable oil, it is complicated to remove the vegetable oil. Plant leaves with chlorophyll or wax have problems in that hydrolases are deactivated during removal of chlorophyll and wax.

The plant extract in the second step may be an extract obtained with at least one solvent selected from the group consisting of a lower alcohol of C1 to C4, acetone, ethyl acetate, and hexane. The lower alcohol of C1 to C4 may be methanol, ethanol, propanol, isopropanol, butanol, or so on.

In addition, the plant extract may be a fraction obtained by subjecting a plant to extraction with at least one solvent selected from the group consisting of a lower alcohol of C1 to C4, acetone, ethyl acetate, and hexane, concentrating the extract, and adding an organic solvent to the concentrate.

So long as it contains a saponin, any plant may be available for preparing the plant extract. The plant extract may be an extract from plants belonging to the families Ranunculaceae, Araliaceae, Dioscoreaceae, Leguminosae, Cucurbitaceae, Compositae, Rosaceae, Liliaceae, Rubiaceae, Rhamnaceae, and Caryophyllaceae, without limitations thereto. Preferably, the plant extract may be an extract from at least one selected from the group *Pulsatilla koreana, Pulsatilla chinensis, Pulsatilla cernua, Anemone raddeana, Aralia elata, Akebia quinata, Lonicera* species, and *Patrinia scabiosifolia*, more preferably from the group consisting of *Anemone raddeana, Lonicera species, Pulsatilla koreana* and *Aralia elata*, and most preferably from *Lonicera* species.

The organic solvent may be a lower alcohol of C1 to C4, ethyl acetate, hexane, or acetone. The lower alcohol of C1 to C4 may be methanol, ethanol, propanol, isopropanol, butanol, or so on.

The fermentation in the third step is to hydrolyze glycosyl ester at position 28 in saponins present in plants to form a free acidic functional group, thereby converting the saponins to anticancer saponins having high anticancer activity. The hydrolysis utilizes a hydrolase present in a medium of plant per se in hydrolyzing glycosyl ester of saponins in the medium of plant per se and the plant extract.

The column chromatography in the fifth step may be selected from silica gel column chromatography, HP-20 column chromatography, RP-18 column chromatography, LH-20 column chromatography, high-performance liquid chromatography (HPLC), and reverse phase HPLC.

The organic solvent in the fourth step or the sixth step may be a lower alcohol of C1 to C4, ethyl acetate, hexane, or acetone. The lower alcohol of C1 to C4 may be methanol, ethanol, propanol, isopropanol, butanol, or so on.

The *Anemone raddeana* and *Lonicera* species extract may have 15-110 folds improved contents of anticancer saponins.

The contents of anticancer saponins were obtained by analyzing the increase rate of anticancer saponins in the extracts from *Anemone raddeana* and *Lonicera* species, which were prepared according to the preparation method of the present disclosure and are highly rich in anticancer saponins, relative to those from *Anemone raddeana* and *Lonicera* species that had not undergone the fermentation process.

The anticancer saponin may be a monodesmoside having hederagenin, oleanolic acid, betulinic acid, or 23-hydroxybetulinic acid as the aglycone moiety thereof, with a free acidic functional group at position 28. Preferably, the anticancer saponin may be at least one selected from the group consisting of hederagenin 3-O-α-L-rhamnopyranosyl-(1→2)-[β-D-glucopyranosyl-(1→4)]-α-L-arabinopyranoside, hederagenin 3-O-β-D-glucopyranosyl-(1→4)-β-D-glucopyranosyl-(1→3)-α-L-rhamnopyranosyl-(1→2)-α-L-arabinopyranoside, oleanolic acid 3-0-α-L-rhamnopyranosyl-(1→2)-[β-D-glucopyranosyl-(1→4)]-α-L-arabinopyranoside, and hederagenin 3-O-β-D-glucopyranosyl-(1→3)-α-L-rhamnopyranosyl-(1→2)-α-L-arabinopyranoside, and more preferably from the group consisting of hederagenin 3-O-β-D-glucopyranosyl-(1→4)-β-D-glucopyranosyl-(1→3)-α-L-rhamnopyranosyl-(1→2)-α-L-arabinopyranoside, oleanolic acid 3-0-α-L-rhamnopyranosyl-(1→2)-[β-D-glucopyranosyl(1→4)]-α-L-arabinopyranoside, and hederagenin 3-O-β-D-glucopyranosyl-(1→3)-α-L-rhamnopyranosyl-(1→2)-α-L-arabinopyranoside.

The *Anemone raddeana* and *Lonicera* species extract may further comprise a medium of plant per se or a plant extract, each containing a saponin.

So long as it contains saponin, any medium of plant per se may be further included. Examples of the medium of plant per se include mediums of plants per se belonging to the families Ranunculaceae, Araliaceae, Dioscoreaceae, Leguminosae, Cucurbitaceae, Compositae, Rosaceae, Liliaceae, Rubiaceae, Rhamnaceae, and Caryophyllaceae, but are not limited thereto. The medium of plant per se may be preferably a medium of at least one plant per se selected from the group consisting of *Pulsatilla koreana, Pulsatilla chinensis, Pulsatilla cernua, Aralia elata, Akebia quinata, Anemone raddeana, Lonicera* species, and *Patrinia scabiosifolia*, more preferably from *Pulsatilla koreana* and *Akebia quinata*, and most preferably from *Pulsatilla koreana*.

So long as it contains a saponin, any plant extract may be further included. Examples of the plant extract include extracts from plants belonging to the families Ranunculaceae, Araliaceae, Dioscoreaceae, Leguminosae, Cucurbitaceae, Compositae, Rosaceae, Liliaceae, Rubiaceae, Rhamnaceae, and Caryophyllaceae, but without limitations thereto. The plant extract may be preferably an extract from at least one plant selected from the group consisting of *Pulsatilla koreana, Pulsatilla chinensis, Pulsatilla cernua, Aralia elata, Akebia quinata, Lonicera* species, and *Patrinia scabiosifolia*, and more preferably from the group consisting of *Pulsatilla koreana* and *Aralia elata*.

The composition comprising the *Anemone raddeana* and *Lonicera* species extract as an active ingredient may be a pharmaceutical composition.

The pharmaceutical composition may further comprise a conventional anticancer agent.

So long as it is currently used, any anticancer agent may be included. The anticancer agent may be preferably derived from plants. Examples of the anticancer agent include vinblastine, vincristine, vinorelvine, paclitaxel, docetaxel, camptothecin, topotecan, irinotecan, belotecan, podophyllotoxin, etoposide, teniposide, deoxypodophyllotoxin, bupleurotoxin, and cymarilic acid, with preference for deoxypodophyllotoxin, bupleurotoxin, and cymarilic acid.

Deoxypodophyllotoxin, bupleurotoxin, and cymarilic acid are anticancer agents inhibiting angiogenesis and a combination of the composition of the present disclosure and the anticancer agent exhibits remarkably improved anticancer activity.

The pharmaceutical composition may comprise the *Anemone raddeana* and *Lonicera* species extract and a pharmaceutically acceptable excipient or carrier.

The pharmaceutical composition may be formulated into oral dosage forms such as powders, granules, tablets, capsules, suspensions, emulsions, syrups, aerosols, etc., topical agents, suppositories, and sterile injections according to typical methods. Pharmaceutically acceptable carriers, excipients, and diluents that can be contained in the pharmaceutical composition includes lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. When the composition is formulated, diluents or excipients, such as a filler, an extender, a binder, a humectant, a disintegrant, a surfactant, etc. may be used. Solid formulations for oral administration include tablets, pills, powders, granules and capsules, and can be prepared by mixing the *Anemone raddeana* and *Lonicera* species extract of the present disclosure with one or more excipients such as starch, calcium carbonate, sucrose, lactose or gelatin. Also lubricants such as magnesium stearate and talc can be used instead of simple excipients. Liquid formulations for oral administrations include a suspension, a liquid and solution, an emulsion, a syrup, and frequently used water, liquid paraffin and other excipients such as humectants, sweeteners, aromatics and preservatives can also be used. In the formulations for non-oral administration, a sterilized aqueous solution, a non-aqueous solvent, a suspension, an emulsion, a freeze-dried formulation, a rectal suppository and a transcutaneous formulation are included. Propylene glycol, polyethylene glycol, vegetable oil, such as olive oil, and injectable esters, such as ethyloleate, can be used as a non-aqueous solvent or a suspension. The base for suppository includes witepsol, macrogol, tween 61, cacao oil, laurin oil, glycerol and gelatin.

The administration dose of the pharmaceutical composition may vary depending various factors including the age, sex and body weight of a subject to be treated, particular disease or pathological condition to be treated, severity of disease or pathological condition, administration route and the judgment of a prescriber. Determination of the effective dose may be made by those skilled in the art based on the above-mentioned factors. In general, the active ingredient may be administered in a dose of about 0.01 mg/kg/day to 2,000 mg/kg/day, and particularly about 0.1 mg/kg/day to 500 mg/kg/day. The administration may be carried out once a day or several times in a divided dose a day. The above dose is not intended to restrict the scope of the present invention in any way.

The pharmaceutical composition may be administered to mammals, such as rats, domestic animals, and humans, via various routes. All manners of administration may be predicted, and for example, the administration may be carried out through oral, rectal, intravenous, intramuscular, subcutaneous, endometrial, intracerebroventricular injection.

As used herein, the term "cancer", also called malignant tumor, refers to a lump that has abnormally grown due to autonomous overgrowth of the body's tissue and which invades to neighboring tissues, rapidly grows, and diffuse or metastasize to various parts of the body, finally threatening the life. Cancer includes carcinoma and sarcoma.

The cancer may be a solid cancer. Preferably, examples of the cancer include stomach cancer, liver cancer, colon cancer, breast cancer, lung cancer, non-small cell lung cancer, pancreatic cancer, skin cancer, head and neck cancer, melanoma, uterine cancer, ovarian cancer, large intestine cancer, small intestine caner, rectal cancer, endometrial cancer, cervical cancer, vaginal cancer, prostate cancer, testis cancer, esophageal cancer, bile duct cancer, malignant lymphoma, bladder cancer, gallbladder cancer, endocrine cancer, prostate cancer, adrenal cancer, thymoma, mesothelioma, renal cancer, brain cancer, tumors of central nervous system, brainstem glioma, and pituitary adenoma.

In addition, the composition comprising an *Anemone raddeana* and *Lonicera* species extract as an active ingredient may be a health functional food.

The health functional food may comprise a sitologically acceptable auxiliary food additive in addition to the *Anemone raddeana* and *Lonicera* species extract.

The health functional food may be in the form of a tablet, a capsule, a pill, or a liquid. Examples of the foods to which the extract may be added according to the present disclosure include various foods, beverages, gum, teas, vitamin complexes, health functional foods, etc.

Advantageous Effects

The present disclosure pertains to a composition comprising an *Anemone raddeana* and *Lonicera* species extract highly rich in anticancer saponins as an active ingredient for prevention or treatment of cancer, and a preparation method therefor. In the present disclosure, saponins contained in an *Anemone raddeana* and *Lonicera* species extract are converted to anticancer saponins having high anticancer activity and the extract prepared in the present disclosure is found to exhibit a potent anticancer activity.

As a result, it is expected that the *Anemone raddeana* and *Lonicera* species extract highly rich in anticancer saponins according to the present disclosure can be used to develop a medicinal product for treatment of cancer.

BRIEF DESCRIPTION OF THE DRAWINGS

FIG. 1 shows anticancer activities of the compositions comprising an *Anemone raddeana* and *Lonicera* species extract as an active ingredient according to the present disclosure.

MODE FOR CARRYING OUT THE INVENTION

Hereinafter, preferred examples of the present disclosure will be described in detail. The present disclosure may, however, be embodied in many different forms and should not be construed as being limited to the examples set forth herein. Rather, these examples are provided so that this disclosure will be thorough and complete and will fully convey the concept of the invention to those skilled in the art.

Experimental Example 1. Preparation of Plant Extract and Medium of Plant Per Se

Selection was made of saponin-containing target plants including *Pulsatilla koreana, Pulsatilla chinensis, Pulsatilla cernua, Anemone raddeana, Aralia elata, Akebia quinata, Patrinia scabiosifolia, Lonicera* species (*Lonicera* sp.), which each have hederagenin or oleanolic acid as the aglycone moiety thereof.

Available portions of the plants were roots from *Pulsatilla koreana, Pulsatilla chinensis, Pulsatilla cernua, Anemone raddeana*, and *Patrinia scabiosifolia*, leaves from *Aralia elata*, seeds or fruits from *Akebia quinata*, and *Lonicera japonica* flowers from *Lonicera* species.

Experimental Example 1-1. Preparation of Plant Extract

1) *Pulsatilla chinensis* Extract (Pc Extract)

Roots of *Pulsatilla chinensis* were pulverized into powder in a pulverizer. To 100 g of root powder of *Pulsatilla chinensis* was added 500 ml of 70% (v/v) ethanol, followed by reflux for 4 hours while stirring. After reflux, a filtrate was separated by filtration through a filter and stored. The plant residues were added with 500 ml of 70% (v/v) methanol and refluxed for 4 hours to separate an additional filtrate which was pooled with the previous filtrate. The 70% (v/v) methanol extract thus obtained was dried in a vacuum and the resulting dried extract was mixed with 70 ml of 95-100% (v/v) ethanol. Only the ethanol layer was separated by filtration and dried to secure a *Pulsatilla chinensis* extract (6.4 g).

2) *Pulsatilla cernua* Extract (Pcer Extract)

A *Pulsatilla cernua* extract (5.9 g) was obtained from *Pulsatilla cernua* roots in the same manner as the preparation method for 1) *Pulsatilla chinensis* extract in Experimental Example 1-1.

3) *Anemone raddeana* Extract (Ar Extract)

An *Anemone raddeana* extract (4.1 g) was obtained from *Anemone raddeana* roots in the same manner as the preparation method for 1) *Pulsatilla chinensis* extract in Experimental Example 1-1.

4) *Patrinia scabiosifolia* Extract (Ps Extract)

A *Patrinia scabiosifolia* (4.0 g) was obtained from *Patrinia scabiosifolia* roots in the same manner as the preparation method for 1) *Pulsatilla chinensis* extract in Experimental Example 1-1.

5) *Aralia elata* Extract (Ae Extract)

Young *Aralia elata* leaves taken in late April were dried in a shade place and finely cut. After being mixed with 300 ml of 95-100% (v/v) of methanol, 100 g of the cut leaves was ground in a mixer and then refluxed for 5 hours using an extractor while stirring. Thereafter, only the methanol layer was separated by filtration using a filter. The plant residues were added with 300 ml of 95% (v/v) methanol and refluxed for 5 hours to separate an additional methanol layer which was then pooled with the previous methanol layer. The methanol extract thus obtained was concentrated to a volume of about 200 ml to which 200 ml of hexane was added and shaken for 10 minutes. The mixture was left and the methanol layer thus formed was separated to give a primary methanol fraction. The primary methanol fraction was added again with 200 ml of hexane, shaken for 10 min, and left. The methanol layer thus formed was separated to secure a secondary methanol fraction. The secondary methanol fraction was concentrated and dried to obtain a solid. The solid was mixed with 70 ml of 100% (v/v) ethanol and left for 30 min, followed by filtration to separate the ethanol layer only. The separated ethanol layer was dried to afford an *Aralia elata* extract (3.7 g).

6) *Akebia quinata* Extract (Aq Extract)

In 400 ml of hexane, 100 g of *Akebia quinata* seeds was ground using a mixer and then left. The hexane layer was separated and filtered to remove hexane. The filtrate free of hexane was mixed with 400 ml of 95% (v/v) methanol and refluxed for 4 hours with an extractor while stirring. After reflux, only the methanol layer was separated by filtration using a filter. The plant residues were added with 500 ml of 95% (v/v) methanol and refluxed for 4 hours to separate an additional methanol layer which was then pooled with the previous methanol layer. The methanol extract thus obtained was concentrated to a volume of about 300 ml to which 300 ml of hexane was added and shaken for 10 minutes. The mixture was left and the methanol layer thus formed was separated by removing the hexane layer. The separated methanol layer was dried in a vacuum. The residue thus obtained was mixed with 70 ml of 100% (v/v) ethanol, left for a predetermined time, and filtered to separate the ethanol layer only. This ethanol layer was dried to afford an *Akebia quinata* extract (4.4 g).

7) *Lonicera* sp. Extract (Lj Extract)

Flowers of *Lonicera japonica* were used. After being mixed with 300 ml of 95% (v/v) of methanol, 100 g of the flowers was ground in a mixer and then refluxed for 3 hours using an extractor. Thereafter, only the methanol layer was separated by filtration using a filter. The plant residues were added with 300 ml of 100% (v/v) methanol and refluxed for 3 hours to separate an additional methanol layer which was then pooled with the previous methanol layer. The methanol extract thus obtained was concentrated to a volume of about 200 ml to which 200 ml of hexane was added and shaken for 10 minutes. The mixture was left and the methanol layer thus formed was separated by removing the hexane layer to give a primary methanol fraction. The primary methanol fraction was added again with 200 ml of hexane, shaken for 10 min, and left. The methanol layer thus formed was separated to secure a secondary methanol fraction. The secondary methanol fraction was concentrated and dried to obtain a solid. The solid was mixed with 70 ml of 100% (v/v) ethanol and left for 30 min, followed by filtration to separate the ethanol layer only. The separated ethanol layer was dried to afford a *Lonicera* sp. extract (3.9 g).

Experimental Example 1-2. Preparation of Medium of Plant Per Se

Saponins in plant exist mainly as glycosides. Particularly, in saponins having hederagenin, oleanolic acid, betulinic acid, and 23-hydroxybetulinic acid as aglycone moieties, the acidic group at position 28 is in the form of glycosyl ester. Thus, the ester group must be hydrolyzed in order to obtain anticancer saponins. Chemical hydrolysis may not only influence on the structure of saponins, but also requires complicate separation processes, thus decreasing in economic advantage. In the present disclosure, advantage was taken of the hydrolysis of the ester group by a hydrolase present in plants during the isolation of saponins glycosides from the plants, and a medium of plant per se was prepared with reference to the technical disclosure set forth in Korean Patent Number 0628334 issued to the present inventors.

Any of the plants used in Experimental Example 1 may be available for preparing a medium of plant per se. For seeds rich in vegetable oil such as *Akebia quinata* seeds, however, it is complicated to remove the vegetable oil. For *Aralia*

*elata* leaves, hydrolases may be deactivated during removal of chlorophyll and wax. Hence, the present disclosure utilized *Pulsatilla koreana* roots, *Anemone raddeana* roots, and *Akebia quinata* fruits.

1) Medium of *Pulsatilla koreana* Per Se (Pk Medium)

Fresh *Pulsatilla koreana* roots were washed with water and peeled before being finely cut. In 200 ml of distilled water cooled to 4° C., 100 g of the finely cut *Pulsatilla koreana* roots was ground using a mixer. The roots ground with a mixer were sonicated for 10 minutes at high frequency with a sonicator to prepare a medium of *Pulsatilla koreana* per se.

2) Medium of *Anemone raddeana* Per Se (Ar Medium)

A medium of *Anemone raddeana* per se was prepared from *Anemone raddeana* roots in the same manner as the preparation method for 1) medium of *Pulsatilla koreana* per se in Experimental Example 1-2.

3) Medium of *Akebia quinata* Per Se (Aq Medium)

Use was made of *Akebia quinata* fruits that remained undivided. In 200 ml of distilled water cooled to 4° C., 100 g of *Akebia quinata* fruits was ground using a mixer. The fruits ground with a mixer was sonicated for 5-10 minutes at high frequency using a sonicator to prepare a medium of *Akebia quinata* per se.

Example 1. Preparation of Extract Containing High Concentration of Anticancer Saponin An extract containing a high concentration of anticancer saponins according to the present disclosure was prepared using the plant extracts and media of plant per se prepared in Experimental Example 1. In this regard, the media of plant per se were used immediately after being prepared.

Example 1-1. Preparation of an *Anemone raddeana* and *Lonicera* Species Extract A mixture of 2) medium of *Anemone raddeana* per se (Ar medium) in Experimental Example 1-2 and 3.9 g of 7) *Lonicera* species extract (Lj extract) in Experimental Example 1-1 was fermented at 37° C. for 2 hours while stirring. The fermented product was cooled to room temperature, added with 400 ml of 95% (v/v) methanol, and stirred at room temperature for 12 hours. Thereafter, a filtrate was separated using a filter and stored. The solid residue after filtration was added with 400 ml of 95% (v/v) methanol and reacted in the same manner as described above to obtain a filtrate. The filtrates obtained twice were combined and concentrated. The concentrate thus obtained was dried using a desiccator. The resulting solid residue was mixed with 70 ml of 100% (v/v) ethanol and left for a predetermined time, followed by filtration through a filter to separate only the ethanol layer. The separated ethanol layer was transferred into a pyrogen-free vessel and dried to give 5.4 g of a solid.

In 10 ml of distilled water was dissolved 2 g of the solid which was then left for 20 min, followed by filtration through a filter. The filtrate thus obtained was stabilized with water and added and adsorbed to 300 g of diaion HP-20 resin packed in a column (column size 5×80 cm). After the column was washed by passing 1,500 ml of distilled water over 2 hours therethrough, elution was conducted by sequentially adding 300 ml of 20% (v/v) methanol and 1,000 ml of 90% (v/v) methanol. The eluates were collected by 20 ml. Drops of the collected eluates were placed on silica gel plates and dried. Afterwards, 10% (v/v) sulfuric acid was sprayed over the plates which were then heated to 150° C. to monitor the appearance of white red colors. Only the eluates that appeared white red were pooled, concentrated, and dried. The solid residue was mixed with 20 ml of 100% (v/v) ethanol and left for a predetermined time, followed by filtration through a filter to separate only the ethanol layer. The separated ethanol layer was transferred into a pyrogen-free vessel and dried to afford an *Anemone raddeana* and *Lonicera* species extract (0.98 g) containing a high concentration of anticancer saponins according to the present disclosure.

Example 1-2. Preparation of *Anemone raddeana*, *Lonicera* Species and *Aralia elata* Extract A mixture of 2) medium of *Anemone raddeana* per se (Ar medium) in Experimental Example 1-2 and 3.9 g of 7) *Lonicera* species extract (Lj extract) and 3.7 g of 5) *Aralia elata* extract (Ae extract) in Experimental Example 1-1 was fermented at 37° C. for 2.5 hours while stirring. The fermented product was cooled to room temperature, added with 500 ml of 95% (v/v) methanol, and stirred at room temperature for 12 hours. Thereafter, a filtrate was separated using a filter and stored. The solid residue after filtration was added with 500 ml of 95% (v/v) methanol and reacted in the same manner as described above to obtain a filtrate. The filtrates obtained twice were combined and concentrated. The concentrate thus obtained was dried using a desiccator. The resulting solid residue was mixed with 100 ml of 100% (v/v) ethanol and left for a predetermined time, followed by filtration through a filter to separate only the ethanol layer. The separated ethanol layer was dried to form a solid to which 70 ml of 100% (v/v) ethanol was then added. Only the ethanol layer was separated by repeating the above process. The separated ethanol layer was transferred into a pyrogen-free vessel and dried to give 7.9 g of a solid.

From 2 g of the solid, an *Anemone raddeana*, *Lonicera species*, and *Aralia elata* extract (1.09 g) containing a high concentration of saponins according to the present disclosure was prepared in the same manner as with the diaion HP-20 column in Example 1-1.

Example 1-3. Preparation of *Anemone raddeana*, *Lonicera* Species, and *Pulsatilla koreana* Extract A mixture of 1) *Pulsatilla koreana* per se (Pk medium) in Experimental Example 1-2 and 4.1 g of 3) *Anemone raddeana* extract (Ar extract) and 3.9 g of 7) *Lonicera* species extract (Lj extract) in Experimental Example 1-1 was fermented at 37° C. for 2.5 hours while stirring. The fermented product was cooled to room temperature, added with 500 ml of 95% (v/v) methanol, and stirred at room temperature for 12 hours. Thereafter, a filtrate was separated using a filter and stored. The solid residue after filtration was added with 500 ml of 95% (v/v) methanol and reacted in the same manner as described above to obtain a filtrate. The filtrates obtained twice were combined and concentrated. The concentrate thus obtained was dried using a desiccator. The resulting solid residue was mixed with 100 ml of 100% (v/v) ethanol and left for a predetermined time, followed by filtration through a filter to separate only the ethanol layer. The separated ethanol layer was transferred into a pyrogen-free vessel and dried to give 8.1 g of a solid.

From 2 g of the solid, an *Anemone raddeana*, *Lonicera species*, and *Pulsatilla koreana* extract (1.09 g) containing a high concentration of saponins according to the present disclosure was prepared in the same manner as with the diaion HP-20 column in Example 1-1.

Comparative Example 1. Preparation of Comparative Extracts Containing Anticancer Saponins

Comparative Example 1-1. Preparation of *Pulsatilla koreana* Extract 1

After 1) the medium of *Pulsatilla koreana* per se (Pk medium) in Experimental Example 1-2 was prepared, *Pulsatilla koreana* extract 1 to be compared was prepared in the same manner as in Example 1-1 with the exception that the fermentation process was excluded.

Comparative Example 1-2. Preparation of *Pulsatilla koreana* Extract 2

After 1) the medium of *Pulsatilla koreana* per se (Pk medium) in Experimental Example 1-2 was fermented at 37° C. for 2 hours while stirring, the subsequent process was conducted in the same manner as in Example 1-1 to prepare *Pulsatilla koreana* extract 2 to be compared.

Comparative Example 1-3. Preparation of *Anemone raddeana* Extract 1

After 2) the medium of *Anemone raddeana* per se (Ar medium) in Experimental Example 1-2 was prepared, *Anemone raddeana* extract 1 to be compared was prepared in the same manner as in Example 1-1 with the exception that the fermentation process was excluded.

Comparative Example 1-4. Preparation of *Anemone raddeana* Extract 2

After 2) the medium of *Anemone raddeana* per se (Ar medium) in Experimental Example 1-2 was fermented at 37° C. for 2 hours while stirring, the subsequent process was conducted in the same manner as in Example 1-1 to prepare *Anemone raddeana* extract 2 to be compared.

Comparative Example 1-5. Preparation of *Lonicera* Species Extract

A *Lonicera* species extract to be compared was prepared in the same manner as for 7) *Lonicera* species extract (Lj extract) in Experimental Example 1-1 with the exception that the fermentation process of Example 1-1 was excluded.

Comparative Example 1-6. Preparation of *Pulsatilla koreana* and *Anemone raddeana* Extract The 1) medium of *Pulsatilla koreana* per se (Pk medium) in Experimental Example 1-2 was mixed 4.1 g of 3) *Anemone raddeana* extract (Ar extract) in Experimental Example 1-1, followed by fermentation at 37° C. for 2 hours while stirring. The subsequent process was conducted in the same manner as in Example 1-1 to prepare a *Pulsatilla koreana* and *Anemone raddeana* extract to be compared.

Comparative Example 1-7. Preparation of *Pulsatilla koreana* and *Lonicera* Species Extract After 3.9 g of 7) *Lonicera* species extract (Lj extract) in Experimental Example 1-1 was mixed with 1) the medium of *Pulsatilla koreana* per se (Pk medium) in Experimental Example 1-2, the subsequent process was conducted in the same manner as in Example 1-1 to prepare a *Pulsatilla koreana* and *Lonicera* species extract to be compared.

Comparative Example 1-8. Preparation of *Anemone raddeana* and *Lonicera* Species Extract An *Anemone raddeana* and *Lonicera* species extract to be compared was prepared in the same manner as in Example 1-1 with the exception that the fermentation process was excluded.

Experimental Example 2. Content of Anticancer Saponin in Extract

Contents of anticancer saponins in the extracts prepared in Example 1 and Comparative Example 1 were measured by high performance liquid chromatography (HPLC). As anticancer saponins to be measured for contents, selection was made of 1) hederagenin 3-O-α-L-rhamnopyranosyl-(1→2)-[β-D-glucopyranosyl-(1→4)]-α-L-arabinopyranoside (hereinafter referred to as "H-gra"), 2) hederagenin 3-O-β-D-glucopyranosyl-(1→4)-β-D-glucopyranosyl-(1→3)-α-L-rhamnopyranosyl-(1→2)-α-L-arabinopyranoside (hereinafter referred to as "H-g(1→4)g(1→3)ra"), 3) oleanolic acid 3-O-α-L-rhamnopyranosyl-(1→2)-[β-D-glucopyranosyl(1→4)]-α-L-arabinopyranoside (hereinafter referred to as "O-gra") and 4) hederagenin 3-O-β-D-glucopyranosyl-(1→3)-α-L-rhamnopyranosyl-(1→2)-α-L-arabinopyranoside (hereinafter referred to as "H-g(1→3)ra").

In 3.5 ml of methanol for HPLC, 10 mg of each of the extracts prepared in Example 1 and Comparative Example 1 was dissolved, followed by filtration through a 0.45 μm filter. Then, 50 μl of the filtrate was loaded into Spherisorb® SSODS column on which HPLC was performed using a concentration gradient of acetonitrile:distilled water (3.4:6.6→4:6[v/v]) at a flow rate of 1.5 ml/min. As a result, peaks of retention time were detected at 26.5 min for H-g(1→4)g(1→3)ra saponin and at 43.5 min for H-gra saponin. In addition, HPLC was performed in the same condition except for using isocratic elution with acetonitrile:distilled water (4.3:5.7[v/v]). Peaks of retention time were detected at 18.5 min for H-g(1→3)ra saponin and at 27.1 min for 0-gra saponin. From peaks for each saponin, contents of anticancer saponins in each extract were analyzed. The results are summarized in Table 1.

TABLE 1

| | Anticancer saponin content (mg/g) | | | |
| --- | --- | --- | --- | --- |
| Extract | H-gra | H-g (1→4) g (1→3) ra | O-gra | H-g (1→3) ra |
| Example 1-1. *Anemone raddeana* and *Lonicera* species extract | 325 | 205.6 | 155.7 | —* |
| Example 1-2. *Anemone raddeana*, *Lonicera* species and *Aralia elata* extract | 261.4 | 146.3 | 133.3 | 109.1 |
| Example 1-3. *Anemone raddeana*, *Lonicera* species and *Pulsatilla koreana* extract | 255.5 | 156.1 | 209.8 | 92.3 |
| Comparative Example 1-1. *Pulsatilla koreana* extract 1 | 2.2 | 0.4 | 1.3 | 1.1 |
| Comparative Example 1-2. *Pulsatilla koreana* extract 2 | 330 | 63.69 | 33 | 82.2 |
| Comparative Example 1-3. *Anemone raddeana* extract 1 | 4.5 | — | 3.2 | — |
| Comparative Example 1-4. *Anemone raddeana* extract 2 | 330 | | 233.9 | — |

TABLE 1-continued

| Extract | Anticancer saponin content (mg/g) | | | |
|---|---|---|---|---|
| | H-gra | H-g (1→4) g (1→3) ra | O-gra | H-g (1→3) ra |
| Comparative Example 1-5. *Lonicera* species extract | — | 10.5 | — | — |
| Comparative Example 1-6. *Pulsatilla koreana* and *Anemone raddeana* extract | 324.3 | 52.1 | 130 | 75.6 |
| Comparative Example 1-7. *Pulsatilla koreana* and *Lonicera* species extract | 207.5 | 177.8 | 27 | 69.4 |
| Comparative Example 1-8. *Anemone raddeana* and *Lonicera* species extract | 4.3 | 9.5 | 3.5 | — |

*: not detected

It was confirmed that when a combination of the plant extract in Experimental Example 1-1 and the medium of the plant per se in Experimental Example 1-2 was hydrolyzed, contents of anticancer saponins listed in Table 1 were increased although not indicated in Table 1.

Example 2. Preparation of Composition Comprising Extract Highly Rich in Anticancer Saponin and Anticancer Agent in Combination Compositions for evaluating anticancer effects upon co-administration of the extracts containing high concentrations of anticancer saponins according to the present disclosure and conventional anticancer agents were prepared.

As an anticancer agent, deoxypodophyllotoxin (DPT) was used. A 3 µg/ml DPT solution was prepared by mixing 1 ml of a solution of 30 mg of DPT in 100 ml of 95% (v/v) ethanol with 99 ml of 95% (v/v) ethanol. This solution was used as a DPT stock.

In addition, 10 mg of each of the extracts highly rich in anticancer saponins of Examples 1-1 to 1-3 was dissolved in 9 ml of physiological saline and then mixed with 1 ml of the 3 µg/ml DPT to prepare compositions of Examples 2-1 to 2-3 as listed in Table 2, below.

TABLE 2

| Example | Composition |
|---|---|
| Example 2-1 | Example 1-1. *Anemone raddeana* and *Lonicera* species extract + DPT |
| Example 2-2 | Example 1-2. *Anemone raddeana*, *Lonicera* species and *Aralia elata* extract + DPT |
| Example 2-3 | Example 1-3. *Anemone raddeana*, *Lonicera* species and *Pulsatilla koreana* extract + DPT |

Experimental Example 3. Anticancer Activity

In order to assay anticancer activities of extracts highly rich in anticancer saponins in Example 1 and Comparative Example 1 and compositions comprising extracts highly rich in anticancer saponins and an anticancer agent in Example 2, solid cancer-induced mouse models were used.

A solid cancer accounts for a mass of cancer cells. There are a variety of solid cancers and thus, it is difficult in terms of time and cost to evaluate anticancer activities against all kinds of solid cancers. In this regard, solid cancer-induced mouse models which had been established by subcutaneously transplanting cancer cells were employed because many researchers had proven the effectiveness of the models.

BDF1 male mice with 4 weeks of age, each weighing 20-23 g, were raised at 22±2° C. in the humidity condition 65±5%. The mice were randomly divided into groups of five. In order to induce the onset of a solid cancer, Lewis lung carcinoma cells (LLC) were subcutaneously transplanted in an amount of $1\times10^6$ cells into the left front armpit of each BDF1 mouse and incubated for 24 hours. After 24 hours, the extracts of Example 1 and Comparative Example 1 or the compositions comprising combinations of extracts and anticancer agent in Example 2 were intraperitoneally injected at a daily dose of 10 mg/kg for two weeks.

A mouse group which was treated with none of the extracts after transplantation of the cancer cells was used as a negative control. When the cancer volume in the negative control reached about 2 cm³, cancer sizes were measured.

Cancer growth inhibition rates were calculated according to the following formula 1. On days 7 and 14 after drug administration, cancer growth inhibition rates were measured and the results are shown in Table 3 below and FIG. 1.

Cancer growth inhibition rate (%)=((average cancer volume in negative control−average cancer volume in administered group)/average cancer volume in negative control)×100  [Formula 1]

TABLE 3

| Extract | Single Dose | | Cancer growth Inhibition Rate (%) | | No. of mouse with cancer extinct |
|---|---|---|---|---|---|
| | Anticancer saponin (mg/kg) | DPT (ng/kg) | Day 9 | Day 14 | |
| Example 1-1. *Anemone raddeana* and *Lonicera* species extract | 10 | — | 55.6 | 74.9 | 0 |
| Example 1-2. *Anemone raddeana*, *Lonicera* species and *Aralia elata* extract | 10 | — | 58.7 | 85.5 | 1 |
| Example 1-3. *Anemone Lonicera raddeana*, *Lonicera* species and *Pulsatilla koreana* extract | 10 | — | 60.8 | 82.9 | 1 |
| Example 2-1. Composition containing extract of Example 1-1 and DPT | 10 | 3000 | 65 | 82 | 1 |
| Example 2-2. Composition containing extract of Example 1-2 and DPT | 10 | 3000 | 60.2 | 95.2 | 3 |
| Example 2-3. Composition containing extract of Example 1-3 and DPT | 10 | 3000 | 76 | 94.3 | 2 |
| Comparative Example 1-1. *Pulsatilla koreana* extract | 10 | — | — | 25 | 0 |
| Comparative Example 1-2. *Pulsatilla koreana* extract 2 | 10 | — | 52.3 | 59.1 | 0 |
| Comparative Example 1-3. *Anemone raddeana* extract 1 | 10 | — | — | 13.3 | 0 |
| Comparative Example 1-4. *Anemone raddeana* extract 2 | 10 | — | — | 57.3 | 0 |

TABLE 3-continued

| Extract | Single Dose | | Cancer growth Inhibition Rate (%) | | No. of mouse with cancer extinct |
| --- | --- | --- | --- | --- | --- |
| | Anticancer saponin (mg/kg) | DPT (ng/kg) | Day 9 | Day 14 | |
| Comparative Example 1-15. *Lonicera species* extract | 10 | — | — | — | 0 |
| Comparative Example 1-6. *Pulsatilla koreana* and *Anemone raddeana* extract | 10 | — | 53.1 | 57.6 | 0 |
| Comparative Example 1-7. *Pulsatilla koreana* and *Lonicera* species extract | 10 | — | 54.5 | 58.7 | 0 |
| Comparative Example 1-8. *Anemone raddeana* and *Lonicera* species extract | 10 | — | — | 15 | 0 |

As is understood from the data of Table 3 and FIG. 1, when extracts of Examples 1-1 to 1-3 and Comparative Examples 1-1 to 1-8 were administered at equal doses, cancer growth inhibition rates were detected at remarkably higher levels on day 14 after administration in the mice administered the extracts of Examples 1-1 to 1-3 than Comparative Examples 1-1 to 1-8. In the mice to which extracts of Examples 1-2 and 1-3 had been administered, the transplanted cancer cells were found to completely die.

In addition, when administered, the compositions of Examples 2-1 to 2-3 in which extracts of Examples 1-1 to 1-3 are combined with the anticancer agent DPT exhibited higher cancer growth inhibition rates than the extracts of Examples 1-1 to 1-3 alone, and increased the number of mice in which the transplanted cancer cells had completely become extinct.

As is understood from the results of Experimental Examples 2 and 3, the composition comprising an *Anemone raddeana* and *Lonicera* species extract alone or in combination with an *Aralia elata* or *Pulsatilla koreana* extract according to the present disclosure has a potent anticancer activity, with increased contents of anticancer saponins of H-g(1→4)g(1→3)ra, O-gra, and H-g(1→3)ra therein. Furthermore, co-administration of the extract of the present disclosure and a conventional anticancer agent was observed to increase anticancer activity.

Therefore, it is expected that the *Anemone raddeana* and *Lonicera* species extract containing high concentrations of anticancer saponins according to the present disclosure can be used to develop an anticancer agent having potent anticancer activity.

Formulation Example 1. Pharmaceutical Formulation

Formulation Example 1-1. Preparation of Tablet

With 20 g of the extract of Example 1-2 according to the present disclosure, 175.9 g of lactose, 180 g of potato starch, and 32 g of colloidal silicate were mixed. The mixture was added with a 10% gelatin solution, ground, and filtered through 14-mesh sieves. The filtrate was dried and mixed with 160 g of potato starch, 50 g of talc, and 5 g of magnesium stearate before being prepared into tablets.

Formulation Example 1-2. Preparation of Injection

A solution of 100 mg of the extract of Example 1-2 according to the present disclosure in 100 ml of physiological saline was filtered through a filter capable of removing germs to afford an injection liquid.

The invention claimed is:

1. A pharmaceutical composition comprising a plant extract as an active ingredient for prevention or treatment of cancer, the plant extract being prepared by a process comprising: i) a first step of adding distilled water to *Anemone raddeana* and performing grinding to prepare a plant medium; ii) a second step of adding an organic solvent to flowers of *Lonicera japonica*, to prepare an extract thereof; iii) a third step of combining the plant medium in the first step with the extract in the second step and fermenting the combination at 37° C. while stirring; iv) a fourth step of adding an organic solvent to the fermented product obtained in the third step to form fractions; v) a fifth step of subjecting the fractions of the fourth step to column chromatography to obtain eluates; and vi) a sixth step of adding an organic solvent to the eluates of the fifth step to obtain fractions and drying the fractions to obtain the plant extract.

2. The pharmaceutical composition of claim 1, wherein the plant medium in the first step is prepared by primarily grinding *Anemone raddeana* in distilled water in a mixer; and secondarily performing grinding by sonication.

3. The pharmaceutical composition of claim 1, wherein an anticancer saponin content of the plant extract is 15 to 110 fold improved relative to the extract from *Anemone raddeana* and flowers of *Lonicera japonica* that had not undergone the fermentation process, and wherein the anticancer saponin is at least one selected from the group consisting of hederagenin 3-O-β-D-glucopyranosyl-(1→4)-β-D-glucopyranosyl-(1→3)-α-L-rhamnopyranosyl-(1→2)-α-L-arabinopyranoside, and oleanolic acid 3-O-α-L-rhamnopyranosyl-(1→2)-[β-D-glucopyranosyl-(1→4)]-α-L-arabinopyranoside.

4. The pharmaceutical composition of claim 1, further comprising an anticancer agent.

5. The pharmaceutical composition of claim 1, wherein the cancer is a solid cancer.

* * * * *